United States Patent
Koley et al.

(10) Patent No.: US 10,266,397 B2
(45) Date of Patent: Apr. 23, 2019

(54) III-V NITRIDE RESONATE STRUCTURE BASED PHOTOACOUSTIC SENSOR

(71) Applicant: University of South Carolina, Columbia, SC (US)

(72) Inventors: Goutam Koley, Anderson, SC (US); Abdul Talukdar, Hillsboro, OR (US)

(73) Assignee: University of South Carolina, Columbia, SC (US)

( * ) Notice: Subject to any disclaimer, the term of this patent is extended or adjusted under 35 U.S.C. 154(b) by 339 days.

(21) Appl. No.: 14/824,269

(22) Filed: Aug. 12, 2015

(65) Prior Publication Data

US 2016/0047781 A1     Feb. 18, 2016

Related U.S. Application Data

(60) Provisional application No. 62/070,038, filed on Aug. 13, 2014.

(51) Int. Cl.
*B01L 3/00*        (2006.01)
*B81C 1/00*        (2006.01)
(Continued)

(52) U.S. Cl.
CPC .......... *B81C 1/0015* (2013.01); *B01L 3/5027* (2013.01); *B01L 3/502707* (2013.01);
(Continued)

(58) Field of Classification Search
CPC .. G01N 29/022; G01N 29/222; G01N 27/128; G01N 21/1702; G01N 2291/014; G01N 29/2418; G01N 29/2425; B01L 2400/0484; B01L 3/5027; B01L 3/502707; B01L 3/502715; B01L 2300/0663;
(Continued)

(56) References Cited

U.S. PATENT DOCUMENTS

| | | | |
|---|---|---|---|
| 6,581,438 B1* | 6/2003 | Hall | B23K 31/02 73/53.01 |
| 7,387,889 B2* | 6/2008 | Manalis | G01N 33/54366 422/51 |

(Continued)

OTHER PUBLICATIONS

DeRoller et al, Characterization of an AlGaN/GaN Electrostatically Actuated Cantilever using Finite Element Method, COMSOL Conference 2010 Boston, slides.*

(Continued)

*Primary Examiner* — Daniel S Larkin
*Assistant Examiner* — David L Singer
(74) *Attorney, Agent, or Firm* — Dority & Manning, P.A.

(57) ABSTRACT

A microcantilever based photoacoustic sensor is generally provided. In one embodiment, the microcantilever includes: a substrate; a GaN layer on the substrate, wherein the GaN layer defines a cantilever extending beyond an edge of the substrate, with a base area of the cantilever defined by the area spanning the edge of the substrate; a heterojunction field effect transistor (HFET) deflection transducer positioned on the cantilever; a pair of electrical contacts, each electrically connected to the HFET deflection transducer; and a microfluidic channel in fluid communication with an analyte reservoir, wherein the analyte reservoir is positioned at the base of the cantilever. A sensing system is also generally provided.

7 Claims, 5 Drawing Sheets

(51) Int. Cl.

| | |
|---|---|
| *G01N 21/17* | (2006.01) |
| *G01N 29/02* | (2006.01) |
| *G01N 29/24* | (2006.01) |
| *H01L 29/20* | (2006.01) |
| *H01L 29/778* | (2006.01) |
| *H01L 29/66* | (2006.01) |
| *G01N 29/22* | (2006.01) |
| *H01L 21/02* | (2006.01) |

(52) U.S. Cl.
CPC ....... *G01N 21/1702* (2013.01); *G01N 29/022* (2013.01); *G01N 29/222* (2013.01); *G01N 29/2425* (2013.01); *H01L 21/0254* (2013.01); *H01L 21/02381* (2013.01); *H01L 21/02439* (2013.01); *H01L 29/66431* (2013.01); *H01L 29/66462* (2013.01); *H01L 29/778* (2013.01); *B01L 2300/0663* (2013.01); *B01L 2300/0877* (2013.01); *B01L 2400/0484* (2013.01); *B81B 2203/0118* (2013.01); *G01N 2291/014* (2013.01); *H01L 29/2003* (2013.01); *H01L 29/7786* (2013.01)

(58) Field of Classification Search
CPC ..... B01L 2300/0877; B81B 2203/0118; B81B 3/0029; B81B 3/0021; B81C 1/0015; H03H 9/2405
USPC .............. 422/81, 82; 438/52; 73/61.49, 643, 73/53.01; 250/338.4; 257/E21.217, 257/E29.089, 415
See application file for complete search history.

(56) References Cited

U.S. PATENT DOCUMENTS

| | | | | |
|---|---|---|---|---|
| 7,825,432 | B2* | 11/2010 | Saxler ............... | H01L 21/02381 257/190 |
| 2004/0115838 | A1* | 6/2004 | Quake ................... | B01D 57/02 436/538 |
| 2006/0093647 | A1* | 5/2006 | Villafana ............. | A61K 31/337 424/426 |
| 2007/0145966 | A1* | 6/2007 | Shekhawat .......... | G01N 29/036 324/71.1 |
| 2008/0011058 | A1* | 1/2008 | Lal ....................... | G01N 29/022 73/54.23 |
| 2010/0033723 | A1* | 2/2010 | Thundat ............. | G01N 21/1702 356/432 |
| 2010/0233792 | A1* | 9/2010 | Begley ................ | F16K 99/0001 435/287.1 |
| 2011/0001392 | A1* | 1/2011 | Masmanidis ......... | B81B 3/0021 310/316.03 |

OTHER PUBLICATIONS

DeRoller et al, Characterization of an AlGaN/GaN Electrostatically Actuated Cantilever using Finite Element Method, Excerpt from the Proceedings of the COMSOL Conference 2010 Boston.*
53rd Electronic Materials Conference and Exhibition, Jun. 22-24, 2011 University of California—Santa Barbara, Santa Barbara, California, pp. 32-33.*
Talukdar et al, High frequency dynamic bending response of piezoresistive GaN microcantilevers, 2012, Applied Physics Letters 101, 252102 (2012).*
Peltola et al, High sensitivity trace gas detection by cantilever enhanced photoacoustic spectroscopy using a mid-infrared continuous-wave optical parametric oscillator, published Apr. 18, 2013 l vol. 21, No. 8 l DOI:10.1364/OE.21.010240 l Optics Express 10240.*
Qazi et al, III-V Nitride based piezoresistive microcantilever for sensing applications, Appl. Phys. Lett. 99, 193508 (2011); doi: 10.1063/1.3657467.*
Quddus, Thesis: III-V Nitride Micro- and Nano-Scale Cantilevers For Multimodal Sensing Applications, Jan. 1, 2013.*
University of South Carolina, III-V Nitride Microcantilever based Photoacoustic Biosensor Reference #: 00978, Nov. 2012.*
Ricciardi et al, Integration of microfluidic and cantilever technology for biosensing application in liquid environment, Biosensors and Bioelectronics 26 (2010) 1565-1570.*
Koskinen et al, Progress in cantilever enhanced photoacoustic spectroscopy, Feb. 8, 2008.*
Howe, National Nanotechnology Infrastructure Network Research Highlights 2012, p. 72.*
Walsh et al, Development of a High-throughput Assay for Monitoring cAMP Levels in Cardiac Ventricular Myocytes, Cardiovasc Pharmaco vol. 53, No. 3, Mar. 2009.*
Talukdar et al, Highly Sensitive III-V Nitride Based Piezoresistive Microcantilever Using Embedded AlGaN/GaN HFET as Ultrasonic Detector, 2012, IEEE.*
Qazi et al, III-V Nitride based piezoresistive microcantilever for sensing applications, Applied Physics Letters 99, 193508 (2011).*
National Science Foundation, Award#1348166 Eager: Novel photoacoustic sensor using piezoresistive GaN microcantilever, Jul. 18, 2013.*
A. G. Bell, American Journal of Science 20, 305 (1880).
Adamson, Brian D., John E. Sader, and Evan J. Bieske. "Photoacoustic detection of gases using microcantilevers." Journal of Applied Physics 106.11 (2009): 114510.
Bryan, Andrea K., et al. "Measurement of mass, density, and volume during the cell cycle of yeast." *Proceedings of the National Academy of Sciences*107,3 (2010): 999-1004.
Changhui Li and Lihong V Wang, "Photoacoustic tomography and sensing in biomedicine," Phys. Med. Biol. 54, R59 (2009).
Cheng, Qi, Robert S. Ross, and Kenneth B. Walsh. "Overexpression of the integrin β 1A subunit and the β 1A cytoplasmic domain modifies the β-adrenergic regulation of the cardiac L-type Ca 2+ current." Journal of molecular and cellular cardiology 36.6 (2004): 809-819.
Galanzha, Ekaterina I., et al. "In vivo, noninvasive, label-free detection and eradication of circulating metastatic melanoma cells using two-color photoacoustic flow cytometry with a diode laser." *Cancer research* 69.20 (2009): 7926-7934.
Godin, Michel, et al. "Using buoyant mass to measure the growth of single cells." Nature methods 7.5 (2010): 387-390.
Kreuzer, L. B. "Ultralow gas concentration infrared absorption spectroscopy." Journal of Applied Physics 42.7 (1971): 2934-2943.
Kuusela, T., et al. "Photoacoustic gas detection using a cantilever microphone and III—V mid-IR LEDs." *Vibrational spectroscopy* 51.2 (2009): 289-293.
Lee, J., et al. "Suspended microchannel resonators with piezoresistive sensors." Lab on a Chip 11.4 (2011): 645-651.
Mallidi, Srivalleesha, Geoffrey P. Luke, and Stanislav Emelianov. "Photoacoustic imaging in cancer detection, diagnosis, and treatment guidance." *Trends in biotechnology* 29.5 (2011): 213-221.
Mühlbauer, Marcus, et al. "Detection of melanoma cells in the blood of melanoma patients by melanoma-inhibitory activity (MIA) reverse transcription-PCR." Clinical cancer research 5.5 (1999): 1099-1105.
Abstract of: Qazi, Muhammad, et al. "III-V Nitride based piezoresistive microcantilever for sensing applications." Applied Physics Letters 99.19 (2011): 193508.
Skin Cancer Facts, American Cancer Society, Apr. 19, 2016, http://www.cancer.org/Cancer/CancerCauses/SunandUVExposure/skin-cancer-facts.
Abstract of: Talukdar, Abdul, Muhammad Qazi, and Goutam Koley. "Highly sensitive III—V nitride based piezoresistive microcantilever using embedded AlGaN/GaN HFET as ultrasonic detector." Device Research Conference (DRC), 2012 70th Annual. IEEE, 2012.
Viator, John. "Photoacoustic detection of circulating melanoma cells in human blood." Newsroom 10.117/2.1200904.1630: 3 pages.
Abstract of: Walsh, Kenneth B., Thomas C. Rich, and Zachary J. Coffman. "Development of a high-throughput assay for monitoring cAMP levels in cardiac ventricular myocytes." Journal of cardiovascular pharmacology 53.3 (2009): 223-230.

(56) References Cited

OTHER PUBLICATIONS

Wang, Yu, et al. "Fiber-laser-based photoacoustic microscopy and melanoma cell detection," Journal of biomedical optics 16.1 (2011): 011014-011014.

Weight, Ryan M., et al. "Photoacoustic detection of metastatic melanoma cells in the human circulatory system." *Optics letters* 31.20 (2006): 2998-3000.

Yin, Guangzhi, Da Xing, and Sihua Yang "Dynamic monitoring of blood oxygen saturation in vivo using double-ring photoacoustic sensor." Journal of Applied Physics 106.1 (2009): 013109.

Innovation Toronto, "Patented photoacoustic invention capable of fast, inexpensive, early detection of melanoma", Jan. 12, 2012, 1 page.

\* cited by examiner

| 118 | 2 nm GaN Layer |
| 128 | 15 nm AlGaN (25% Al) Layer |
| 138 | 1 nm AlN Layer |
| 119 | 1000nm GaN Layer |
| 140 | 300 nm Buffer Layer |
| 112 | 720-800 µm Si (111) Substrate |

III-V NITRIDE RESONATE STRUCTURE BASED PHOTOACOUSTIC SENSOR

PRIORITY INFORMATION

The present application claims priority to U.S. Provisional Patent Application Ser. No. 62/070,038 titled "III-V Nitride Microcantilever Based Photoacoustic Biosensor" of Koley, et al. filed on Aug. 12, 2014, the disclosure of which is incorporated by reference herein.

GOVERNMENT SUPPORT CLAUSE

This invention was made with government support under ECCS-0801435 awarded by the National Science Foundation. The government has certain rights in the invention.

BACKGROUND

Development of ultrasensitive micro- and nano-electromechanical systems (MEMS/NEMS) has resulted in ultrahigh detection sensitivity, offering sub nanometer scale displacement detection, zeptogram level mass sensing, single bio-molecular sensing, and atomic resolution imaging. Micro and nanocantilevers, as MEMS/NEMS transducers, have been used extensively for these sensing applications. Optical transduction of cantilever motion is almost exclusively used to achieve high deflection sensitivity (in the femtometer range), but it suffers from high power requirement, challenges with miniaturization and array based operation. Femtometer scale displacement detection using nanocantilevers operating at several hundred MHz has been demonstrated, but is limited by its challenging fabrication and integration schemes, coupled with complicacies of impedance matching for high frequency signal transmission. Silicon (Si) based piezoresistive microcantilevers have been developed which are easily integrated for array based operation, but have low sensitivity offering displacement resolution in the range of nanometers.

Instead of a simple piezoresistor, embedding a transistor at the base of the microcantilever (henceforth to be called a "piezotransistive" microcantilever) to transduce its deflection is an attractive way to dramatically improve its sensitivity by orders of magnitude, since the gate can be utilized to control the charge carrier density and the mobility of the carriers in the channel.

Recently, metal oxide semiconductor field effect transistor (MOSFET) integrated Si cantilevers have been proposed with the goal of achieving very high deflection sensitivity while avoiding the challenges associated with the aforementioned techniques. Although these microcantilevers showed high sensitivity in the nm range for step deflections, since its high sensitivity supposedly originated from trapping effects in the MOSFET, it is difficult to reproduce these sensors, or operate them at high frequencies. Indeed, Si based piezotransistive microcantilevers are theoretically incapable of exhibiting direct sensitivity enhancement through gate control, since the piezoresistive effects in Si originate from the variation in carrier mobility due to strain related splitting of the conduction band minima energy levels. On the other hand, piezotransistive cantilevers made of piezoelectric materials can directly utilize the charge density variation caused by the deflection induced strain to exhibit high sensitivity with very high repeatability.

Due to strong piezoelectric properties of AlN and GaN, AlGaN/GaN heterojunction, provides a unique avenue to translate the static piezoelectric charge generated at the interface due to applied strain into a change in resistance of the two dimensional electron gas (2DEG) formed at the interface, since the generated piezoelectric charge can proportionately modulate the density of the 2DEG. In addition to changing the carrier density, the applied strain can also change the carrier mobility by changing their effective mass. The utility of AlGaN/GaN heterojunction based piezoresistor (for step bending and dynamic deflection measurements) and piezotransistor (for static deflection measurements) has been demonstrated, however, the effect of gate in enhancing displacement sensitivity down to femtometer range in high frequency dynamic deflection mode, with subsequent applications in unique analyte detection, has never been realized.

SUMMARY

Objects and advantages of the invention will be set forth in part in the following description, or may be obvious from the description, or may be learned through practice of the invention.

A microcantilever based photoacoustic sensor is generally provided. In one embodiment, the microcantilever includes: a substrate; a gallium nitride (GaN) layer on the substrate, wherein the GaN layer defines a cantilever extending beyond an edge of the substrate, with a base area of the cantilever defined by the area spanning the edge of the substrate; a heterojunction field effect transistor (HFET) deflection transducer positioned on the cantilever; a pair of electrical contacts, each electrically connected to the HFET deflection transducer; and a microfluidic channel in fluid communication with an analyte reservoir, wherein the analyte reservoir is positioned at the base of the cantilever.

A sensing system is also generally provided. In one embodiment, the sensing system includes: the microcantilever based photoacoustic sensor of the preceding paragraph and a pulsed infrared laser positioned to direct infrared electromagnetic radiation into the reservoir of the microcantilever based photoacoustic sensor.

A method is also generally provided for detecting an analyte within a medium. In one embodiment, the method includes: flowing the medium without any analyte present through the microfluidic channel of the system of the preceding paragraph with the pulsed infrared laser directing infrared electromagnetic radiation into the reservoir to establish a baseline signal created from baseline cantilever oscillations; flowing an unknown sample containing the medium through the microfluidic channel of the system with the pulsed infrared laser directing infrared electromagnetic radiation into the reservoir to establish a baseline signal; wherein the presence of the analyte in the unknown medium changes the baseline signal.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIGS. 1a-1c sequentially show an exemplary GaN microcantilever being fabricated, with:

FIG. 1a showing microfludic lines being etched and coated with a poly(p-xylylene) polymer (e.g., PARYLENE®);

FIG. 1b showing a thin sapphire rectangular film glued on top of the channel for vacuum encapsulation; and FIG. 1c showing polymer tubing (e.g., TYGON®) lines epoxy glued to polydimethylsiloxane (PDMS) block to connect to the microfluidic channel.

DETAILED DESCRIPTION

Figure 1A:
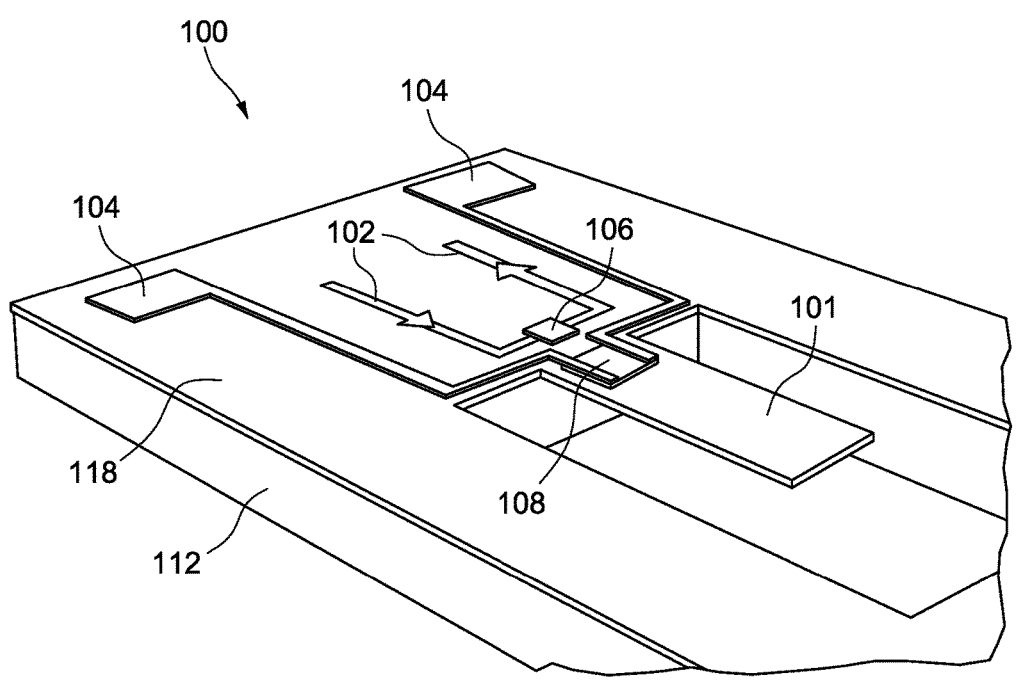

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

In the present disclosure, when a layer is being described as "on" or "over" another layer or substrate, it is to be understood that the layers can either be directly contacting each other or have another layer or feature between the layers, unless expressly stated to the contrary. Thus, these terms are simply describing the relative position of the layers to each other and do not necessarily mean "on top of" since the relative position above or below depends upon the orientation of the device to the viewer.

As used herein, the terms "first", "second", and "third" may be used interchangeably to distinguish one component from another and are not intended to signify location or importance of the individual components.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

Method of fabricating GaN microcantilevers with a AlGaN/GaN heterojunction field-effect transistor (HFET) integrated at the base with very high gauge factor (e.g., greater than about 4500) is provided, along the resulting GaN microcantilevers. Thus, instead of a simple piezoresistor, the transistor imbedded at the base of the microcantilever (henceforth to be called a "piezotransistive" microcantilever) can transduce its deflection is an attractive way to dramatically improve its sensitivity by orders of magnitude, since the gate can be utilized to control the charge carrier density and the mobility of the carriers in the channel. Additionally, fully electronic readout of the deflection of such a microcantilever in both dc and ac conditions is generally provided. Ultrasonic sensing based on III-V Nitride Microcantilever in air and in solid medium is also demonstrated herein using piezoresistive (all electronic) cantilevers. Vacuum enclosed cantilevers are also provided for photoacoustic sensing, such as for photoacoustic detection of biological cells, various cancer cells, especially melanoma cells. Additionally, cell, protein molecules, and DNA identification methods are provided herein based on photoacoustic spectroscopy, along with detection of tumors through photoacoustic microscopy and imaging.

In one embodiment, the present disclosure is generally directed to a highly sensitive and miniaturized sensor, which in certain embodiments is capable of detecting a single analyte in a circulating liquid samples. The sensor utilizes photoacoustic detection techniques to differentiate a targeted analyte from other analytes present in sample in a label-free manner, while system miniaturization can be achieved by using novel and highly sensitive gallium nitride based piezoelectric microcantilever (resembling tiny diving boards) sensors described herein.

Thus, the usage of a highly sensitive microscale and novel III-V Nitride based piezoelectric sensor is generally provided in one embodiment to perform photoacoustic spectroscopy. Also, the usage of the microscale sensor is generally provided to develop an integrated label-free detection platform that can be miniaturized to less than about 1 cm in dimensions. Additionally, the utilization of the concept of enclosing the microcantilever in a high vacuum chamber is generally provided, in one embodiment, to obtain 2-3 orders of magnitude higher sensitivity compared to air operation. Finally, the integration of semiconductor materials with appropriate properties is generally provided, such as III-V Nitrides, which are transparent to probe IR radiation, are used to fabricate the microcantilever sensor (to reduce noise), while Si substrate is used, which offers a mature process technology and useful for future integration of devices on the same chip. The possibility of integrating the IR laser (diode laser chip) in the sensor through heterogeneous integration is also generally provided, since they can be stacked to just increase the thickness of the chip, and not its lateral dimensions which will make it a highly compact photoacoustic spectroscopic detection system and can also have a large array of sensors for simultaneous screening.

A microcantilever based photoacoustic sensor (operating in atmospheric pressure) has also been shown to be 2-3 orders of magnitude higher than a commercially available large area piezoelectric sensor.

In the system disclosed herein, and referring to FIGS. 1a-1c and FIGS. 2a-2b, the photoacoustic sensor 100 is able to uniquely identify molecules if spectroscopy is performed, i.e. vary the wavelength of the incident IR laser 126. Additionally, the microcantilever 101 based photoacoustic sensor 100 can be designed to maximize the detection sensitivity with the ultimate goal of detecting even extremely faint acoustic signal or wave 122 arising from a single cell. In the device, pressure waves are detected when they are created by the melanoma cells 120 in blood as they absorb pulsed IR radiation 130. Thus, more complex simulations and theoretical modeling combining thermal, acoustic, mechanical, and electrical effects will be performed to determine the best design for our sensor. The major sensor parameters to be optimized are the dimensions of the microcantilever 101, the position and dimension of the reservoir 106 for holding analytes. The former would determine two important mechanical parameters, resonance frequency and quality factor, while the latter would determine the signal intensity reaching the microcantilever 101. For the former the targeted value would be about 50 KHz to make sure that fast measurements can be made, while for the latter, a value of greater than about 50,000 in high vacuum is preferred, which would result in high detection sensitivity.

A. Microcantilevers

Microfabricated cantilevers have been used in atomic force microscopy (AFM) for more than 20 years. Cantilevers (like a tiny diving board or beams with one fixed and one free end) have been widely used in recent years as miniaturized, ultrasensitive, and fast-responding sensors for applications in chemistry, physics, biochemistry, and medicine. Microcantilever sensors such as the sensor 100 shown in FIGS. 1a-1c and FIGS. 2a-2b respond not only by bending (static mode) due to the absorption of molecules, change in pressure, temperature, and electrostatic field; as well as shift in resonance frequency, change in amplitude of oscillation 124 (see FIG. 2b) also occurs in dynamic mode. Over a decade, microcantilever based sensing has witnessed an impressive progress due to multi-disciplinary scientific research, evident from the number of publications in the last 10 years. In the last decade, microcantilever based sensors have proved to become a versatile transduction platform for physical parameters, chemical, volatile organic molecules, explosives and biomolecule detection.

Silicon (Si), the most abundant and matured technology, has been always considered as the prime material in semiconductor industries everywhere. However, application of Si has shown limitations in sensing applications in harsh environmental conditions, suffering from low sensitivity and selectivity. Si cannot be used for high temperature applications as it loses the electrical and mechanical reliability at about 500° C. One of the great advantages of the wide band gap semiconductors is their very high mechanical, thermal, chemical and biochemical stability, which offers exciting MEMS/NEMS sensing applications which require reliability, linearity, sensitivity, and selectivity. Moreover, materials with a high Young's modulus can better maintain linearity between applied load and the induced deformation. This particularly demands group-III nitrides, which has high Young's modulus. AlGaN/GaN heterostructures contain a highly conductive two-dimensional electron gas (2DEG) at the interface, which is sensitive to mechanical load, as well as to chemical modification of the surface, and can be used for novel sensing principles. Presence of such a 2DEG is unique to AlGaN/GaN heterostructure, and is attributed to unintentional polarization doping, since it arises because of the strong polarization properties of the nitrides. Among the most common semiconductors AlN (6.13 eV) and GaN (3.42 eV) have much higher bandgap compared to others. Due to such wide bandgaps, their critical electric fields for breakdown are much higher than other III-V semiconductors. Though GaAs has much higher low field mobility, GaN is clearly superior in terms of saturation velocity. Together with high bandgap, high saturation velocity and high mobility makes nitrides ideal contenders for high power microwave application. The presence of a direct and wide bandgap in AlGaN/GaN also make them very suitable for optoelectronic applications, especially in the green, blue, and UV regions of the spectrum, where there are virtually no other contenders.

The intensity of the acoustic pressure waves reaching the cantilever depends on the position of the reservoir, where they are created by the laser spot. The laser wavelength and power (typically ~800 nm, and 100 mW, respectively) producing the best detection sensitivity of the melanoma cells over the background (red blood cells, white blood cells etc.) can be determined. The magnitude of the electrically obtained signal, i.e. electrical sensitivity, is a strong function of the channel resistance which can be tuned with the gate bias of the field-effect transistor (FET). Appropriate gate bias can be optimized (e.g., via modeling and comparison to experimental data) to obtain the best deflection transduction (and sensitivity) possible for the sensor.

Referring to FIGS. 1a-1c, FIGS. 2a-2b, and FIG. 3, the development of the sensor 100 involves the fabrication of a III-V Nitride based microcantilevers 101 with embedded HFETs 108, integration of the microfluidic channels 102 for analyte transport, sealing the sensor in high vacuum, and finally wire bonding to a chip carrier. The microcantilevers 101 can be fabricated through a process that involves separate lithographic steps to define the AlGaN mesa 128, followed by cantilever 101 outline definition, deposition of source/drain and gate metal contacts 104, and finally, through wafer backside Si etching using Bosch process to release the cantilever 101. The microfluidic channel (40×40 µm cross-section) 102 and reservoir 106 near the base of the cantilever 101 can be patterned by introducing a separate fabrication step in the process, in which the GaN layer 118 and the Si or substrate layer 112 are etched to appropriate depth and width. The analyte reservoir 106 can have dimensions suitable such that the cells can be adequately contained within it for the incident laser spot to hit them (e.g., 60×60 µm).

The reservoir walls are, in one embodiment, coated with a poly(p-xylylene) polymer such as PARYLENE® (e.g., at a thickness of about 1 µm) to ensure better acoustic impedance match between the analyte liquid and Si (so that ultrasonic waves can propagate between the two media with low attenuation) as well as to ensure bio-compatibility.

Figure 1B:
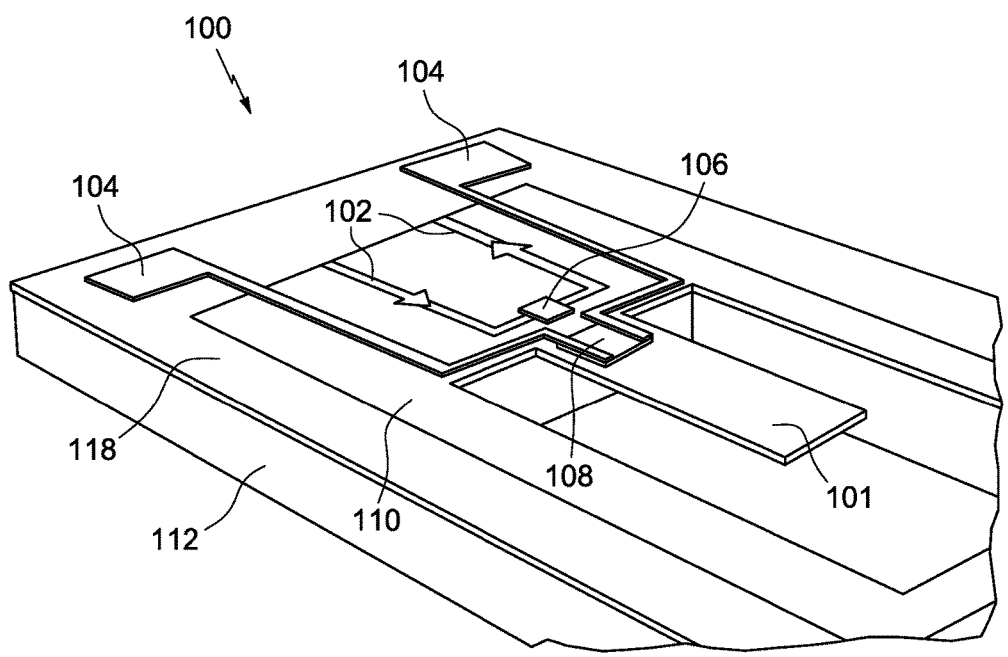
Figure 1C:
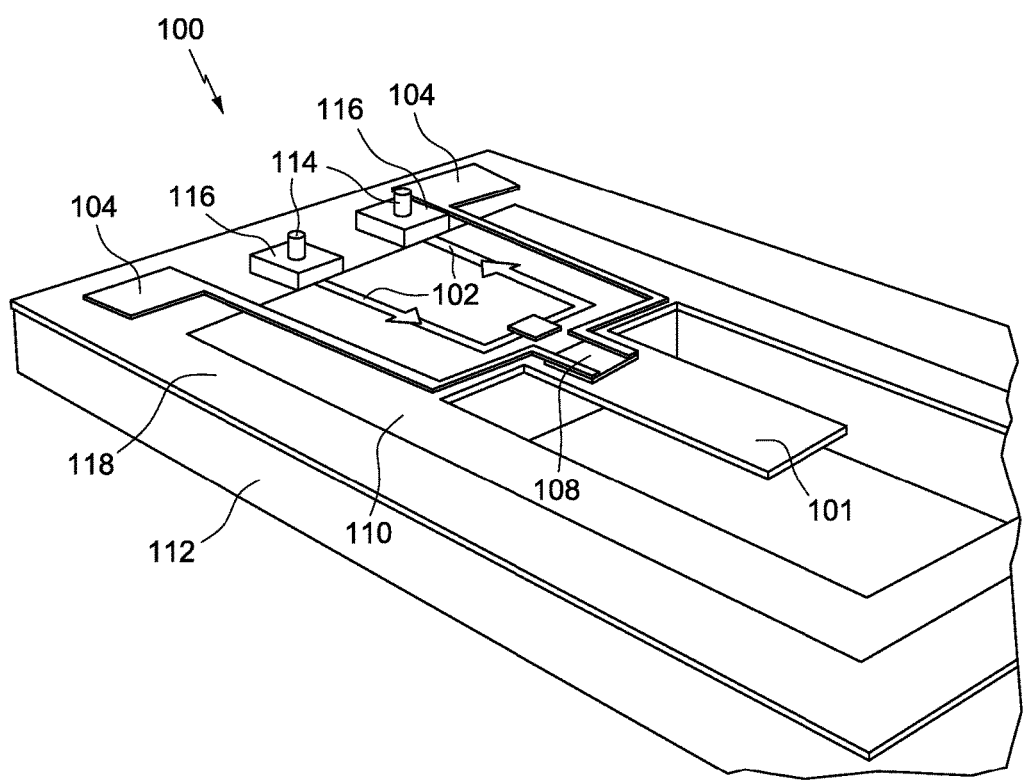

The major fabrication steps for the sensor 100 are shown in FIGS. 1a, 1b, and 1c, with: FIG. 1a showing microfludic lines or channels 102 being etched and coated with a poly(p-xylylene) polymer (e.g., PARYLENE®) onto a microcantilever device 101 (e.g., as shown in FIG. 1c); FIG. 1b showing a thin sapphire rectangular film 110 glued on top of the channel for vacuum encapsulation; and FIG. 1c showing polymer tubing (e.g. TYGON®) lines 114 epoxy glued to polydimethylsiloxane (PDMS) block 116 to connect to the microfluidic lines or channels 102.

In one embodiment, the microcantilever has a length of about 50 µm to about 300 µm, a width of about 25 µm to about 100 µm, and a thickness of about 0.5 µm to about 1.5 µm.

Ultra low vacuum encapsulation is a challenge for MEMS devices. However, vacuum operation of the device is initially achieved by sealing the top layer with an IR transparent sapphire window (e.g., having a thickness of about 100 µm), and attaching a pump outlet to a small orifice in the chip to produce the necessary vacuum. High vacuum (low milliTorr or even µTorr levels) sealing methods can be used to obtain standalone sensor chips with advanced packaging methods such as, solder bonding or even wafer bonding at the bottom surface of the chip (following the initial top layer sealing). Following device fabrication, and vacuum sealing, wire bonding can be done to the leads of the chip carrier. Finally, the external microfluidic lines (to flow the analytes) can be attached to the microfabricated channels using PDMS molding. The sensor can be connected to data acquisition systems (not shown) for testing and measurement.

Melanoma Cancer Cell Detection:

To be clinically relevant, the sensor can detect 1 tumor cell in a background of 106-107 normal blood cells. To simulate circulating melanoma cells in the blood stream, melanoma cells can be suspended in defibrinated bovine blood with a concentration of 1-103 cells/ml. The blood flow can be generated by a syringe pump, and small polymer tubes (e.g., TYGON®) can be epoxy glued to the PDMS molds at the end of the PARYLENE® coated microfluidic channels to circulate the test fluid. The volume flow rate of blood can be set to correspond to a blood flow rate of several cm/s in the microfluidic channels, similar to that in human arteries.

Figure 2A:
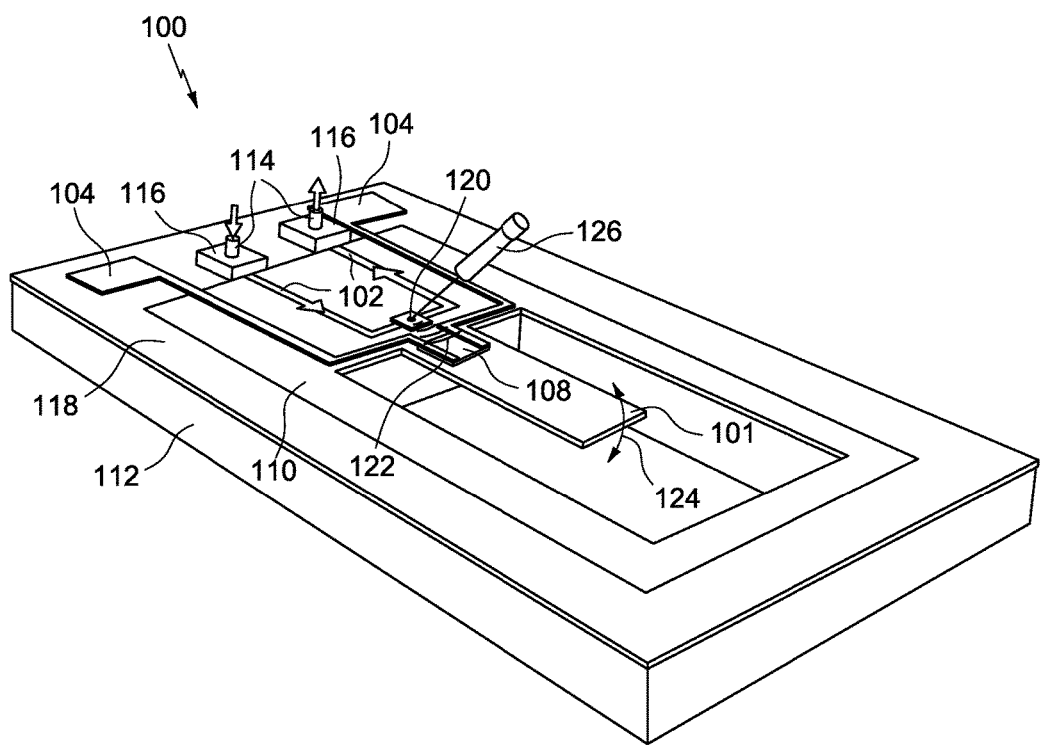
FIG. 2a shows a schematic diagram of an exemplary measurement set up for detection of an analyte in the flowing sample. In this embodiment, the thin sapphire rectangular piece seals the vacuum from the top side, and the bottom of the chip seals to the chip carrier to maintain vacuum around the microcantilever resonator. Signals from the Au contacts will be taken out to a lock-in amplifier.
Figures 2B, 3:
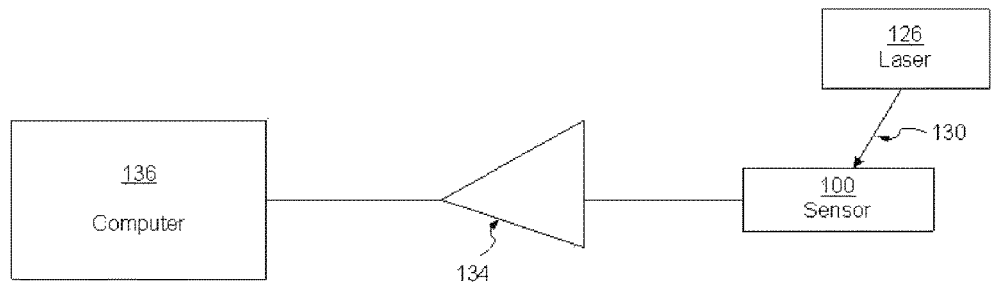
FIG. 2b shows an exemplary system including the microcantilever based photoacoustic sensor, a laser (e.g., pulsed infrared laser positioned to direct infrared electromagnetic radiation into the reservoir of the microcantilever based photoacoustic sensor), an amplifier connected to the sensor, and a general purpose computer connected to the amplifier.
FIG. 3 shows a cross-section of the different layers of the AlGaN/GaN wafer grown on Si (111) substrate, with mesa and cantilever layer as shown, according to Example 1.

Referring to FIGS. 2a and 2b, for detecting the melanoma cells, a 800 nm incident IR laser 126 (the wavelength can be changed as needed to obtain the best resolution) with a power of 100 mW (which can also be changed as needed to obtain the best resolution), can be pulsed on the reservoir 106 at the base of the cantilever 101 at its resonant frequency. The sensor 100's signal can be measured using a lock-in amplifier 134 and recorded by a computer 136 as the melanoma cells 120 absorb pulsed IR radiation 130. The baseline signal can be recorded in presence of normal cells, which increases significantly in presence of melanoma cells, depending on their size and melanin content, as melanoma has two orders of magnitude higher IR absorption coefficient compared to normal blood cells due to presence of melanin. Thus, detection of the passage of individual melanoma cells through the channel is possible, as is detection of the variation in their melanoma content, in real time (on the order of a few ms), which is currently not possible using existing techniques.

Example 1

Fabrications of AlGaN/GaN HFET/MOSHFET (metal-oxide-semiconductor heterojunction field-effect transistor)/ MISHFET (metal-insulator-semiconductor heterojunction field-effect transistor) are well documented. Here, for the first time, the complete fabrication details, issues, and solutions are disclosed of several novel AlGaN/GaN HFET/ MOSHFET/MISHFET embedded GaN microcantilevers. Although the principles and application of different devices vary from each other, but the fabrication processes remain the same.

Wafer Information

Referring to FIG. 3, a six inch AlGaN/GaN wafer grown on Silicon (111) substrate 112 was purchased from NTT ADVANCED TECHNOLOGY CORPORATION, Japan for this work. The wafer was diced into ~44 (1.8 cm by 1.8 cm) square pieces. Before dicing, the wafer was spin coated with photo resist (SHIPLEY 1827) and then baked for 5 mins at 110° C., solely to protect the top surface from any damage may happen during wafer dicing. Silicon substrate 112 (111) of ~720-800 μm thickness was used to grow the AlGaN/GaN layer. A 300 nm buffer layer 140 was used as a transition layer before growing 1 μm undoped GaN layer 119, although a buffer layer of from about 0.5 μm to about 2.5 μm can be used and an undoped GaN layer of from about 500 nm to about 2 μm can be used. Together, this transition layer and the undoped GaN layer form the thickness of the microcantilevers 101. On the top of the GaN layer 119, a thin layer of 1 nm AlN 138 was used to form abrupt junction and better electron confinement in 2DEG by tuning the bandgap. Above that layer, the active layer of AlGaN 128 of 15 nm and 2 nm of GaN cap layer 118 are positioned.

Two 5"×5"×0.09" masks (material: chrome, substrate: quartz) were ordered from PHOTO SCIENCES INC., USA after designing in AutoCAD 2013. There were 7 lithographic layers in the fabrication process (described in details in the next section), all the layers were designed and three copies of each layer were organized in two masks. Three layers (Mesa isolation, GaN cantilever outline, and Backside Si etch) were 1.8 cm by 1.8 cm box equal size of the sample and other three layers were 1.4 cm by 1.4 cm. These layers could be made exact size as others, that makes the alignment task easier but it will consume more space in the mask. If there is plenty space in the mask, it is better to have equal sized layers and also equal to the sample size. The mask was clear field. The back side alignment layer for through wafer Si etching should be mirrored respect to the first two top layers if the design has asymmetry. If it is a symmetric design then mirroring the back side layer would not be necessary. The wafer was diced 1.8 cm by 1.8 cm, though all the devices would fit 1.4 cm sample size. The only reason to have some empty space around the sample for handling with tweezers. Also later in this section, readers will find why it is useful to keep more space around the actual device area. The first two layers specially GaN outline layer and the back side layer should have a '+ sign' for auto dicing each sample into small pieces as it will be really hard to dice the small samples further after final release of cantilevers. While designing the mask, it is easy to start from the GaN outline. After drawing the complete device, then separate each layer and organize according to the size of the mask. PHOTO SCIENCES has its own rules about drawing, and they have to be followed for faster processing. When the mask is made, the mask should be thoroughly checked for any damage, design violation, and sharpness of chrome line.

Microcantilever Design

Positive photo resist (PPR, SC 1827) was used for the first process step, whereas negative photo resist (NPR, NR 71) was used for the rest and NR 5 was used in Bosch process for releasing cantilevers.

Step 1—MESA Outline:

Mesa is the active region on which the AlGaN/GaN HFET is fabricated because the AlGaN/GaN layer has 2DEG throughout the wafer and therefore is conductive all over and needs to be isolated from other patterns on the sample. Only in this layer PPR SC 1827 was used. Plasma-enhanced chemical vapor deposition (PECVD) SiO2 (300-400 nm) was deposited using UNAXIS PECVD tool (deposition rate is 50 nm/min) at the beginning. The oxide was patterned and then etched in Plasma Therm Inductively Coupled Plasma (ICP) tool (etch rate is 180 nm/min, $CHF_3/O_2$ gas). Then used $BCl_3/Cl_2$ based dry etching recipe of GaN in inductively coupled plasma (ICP) to etch 180-200 nm to isolate mesa. Though more than 15 nm of AlGaN etching would be sufficient but over etch is done to ensure complete isolation and also for next alignment purpose (below 100 nm thickness would be harder to see in MA6). After the etching, the photoresist (PR) should be completely removed from top oxide layer following resist remover, oxygen plasma cleaning in Reactive Ion Etcher (RIE), and if necessary dipping in warm sulphuric acid ($H_2SO_4$) for 5-10 minutes. The resist gets crosslinked in ICP, and it becomes literally impossible to remove with just resist remover or acetone. That is why it is better to have the oxide layer protecting the mesa which acts as the hard mask. Otherwise without oxide deposition, mesa etching can still be performed. It is suggested that after mesa etching, the sample should be kept in warm resist remover (MICROPOSIT 1165) for 10-30 minutes and then cleaning the sample with cleanroom swab (soaked in the same remover to make it soft and not to scratch the sample). If this cleaning is not sufficient then oxygen plasma etching would be needed. Keep in mind that, bare AlGaN/GaN mesa should never be exposed in oxygen plasma, otherwise 2DEG would be completely damaged.

Step 2—GaN Cantilever Outline:

In this step, GaN is etched down to make an outline for the cantilever. GaN is etched down in the pocket area up to the substrate where silicon gets exposed. This process was exactly same as step 1. Only difference is the deposited oxide is 1.2 µm thick as the remaining thickness of GaN after etching for mesa in step 1 is about 1.1 µm. Over etching (assuming 2 µm thick GaN) is performed as the etched down GaN has other layers. $BCL_3/Cl_2$ also etches exposed Si (verified using Tencor Profilometer) with same etch rate of 340 nm/min, but this does affect any fabrication process as ultimately the exposed Si will be etched from back completely. In this step and the next ones in this sub-section, negative photo resist (NPR) NR 71 was used. After the etching of oxide similarly as step 1, resist should be removed. After resist removal, wet chemical etching of the oxide is done using Buffered Oxide Etchant (BOE).

Step 3—Ohmic Contact:

For ohmic contact multilayer gate metal stack of Ti (20 nm)/Al (100 nm)/Ti (45 nm)/Au (55 nm) was used. Getting a good ohmic has always been a challenge and multilayer metal stack gives low contact resistance. For a good and easy metal liftoff process, overdevelopment is suggested after post bake of resist as very thin layer of resist would be always present. Also, the extra space surrounding the sample should be used to mount the sample with polyamide film (e.g., KAPTON® tape) in CVC Electron Beam Evaporator's holder. So that the metal does not get deposited on the edges which makes the liftoff very hard and time consuming. The metal liftoff should be done in warm resist remover (RR41), submerging the sample for as long as the unnecessary metal film comes off. After that, the sample was put in fresh warm resist remover for 10-15 minutes and the using soaked (in RR41) cleanroom swab is used to clean the sample by whirling the swab. When satisfied (checking in microscope to ensure no resist is left), the sample should be cleaned with squirting IPA after every successive whirling with swab soaked in resist remover. No oxygen plasma cleaning should be done on the sample with bare AlGaN/GaN mesa. However as the GaN outline has already created several trenches in the sample, resist becomes highly adhesive to the surface, and so warm $H_2SO_4$ treatment can be performed. Every after 1-2 minutes, the sample should be checked to ensure no unwanted liftoff of ohmic contacts is happening. It happens because of thin layer of resist still present underneath the metal contacts. After lift-off is done, the contact is annealed in rapid thermal processing (RTP) at 825° C.

Step 4—Schottky Gate Formation:

If the aim is to design simple piezoresistor then this step should be skipped. In this Example, the designed microcantilevers have many varieties in the FET part, where the samples are processed with or without gate dielectric. Liftoff process was followed to reduce the processing time and one lithography step which involves depositing dielectric materials and then pattern the gate layer to etch away dielectrics from other areas on the sample. However, liftoff process eliminates that need and after patterning the sample with resist, gate dielectric can be deposited followed by gate metal and finally lift off the resist as described in previous step. To create high Schottky barrier with nitride surface, higher work function Schottky contacts are needed and both Pt and Ni are ideal choices for Schottky gate contact. Ni is a preferred choice due to its higher adhesion property with nitrides and can be operable up to 600° C. Therefore a Ni/Au metal stack for Schottky contacts for the HFET gates.

Devices were fabricated without dielectric (HFET), with Plasma Enhanced Chemical Vapor Deposition (PECVD) of $SiO_2$ (MOSHEFT structure), Pulsed Laser Deposition (PLD) of Boron Nitride (BN), and Atomic Layer Deposition (ALD) of $Al_2O_3$ (MISHEFT structure). PECVD oxide is the mostly used gate dielectric which reduces the leakage by several orders as HFET has high gate leakage. The film thickness was 5 nm. For PECVD, 5 nm of oxide was deposited at 100° C. The usual recipe and the UNAXIS PECVD tool would not allow deposition below 250° C. but at that temperature the resist will burn and contaminate the chamber which is not permissible. So if not possible to use the recipe with lower temperature, one has to follow the etching of oxide film with an added litho step. In case of atomic layer deposition (ALD), 5 nm of $Al_2O_3$ was deposited with thermal oxide recipe at 100° C. The deposition rate is 1 Å/cycle which takes more than an hour to deposit 5 nm film. This longer duration hard bakes the resist and eventually impossible to lift off especially with smaller feature size. The only option would be to have the film deposited first and the follow the etching procedure. Although devices with oxide and BN were fabricated, the $Al_2O_3$ deposited devices were not continued for further processing due to limitation of time.

Step 5—Probe Contact:

Large metal pads (250 µm by 250 µm) are deposited for characterization which connects to the drain, source, gate and cantilever tip. Gold with adhesion layer of Ti was used for this metal deposition step. The mask layout has two probe layers with long contact and short contact. Long contacts are helpful for microfluidic channel integration, vacuum sealing of the sample, and utilizing fabricated micro-canals/discs which are patterned in step 2. The lift off process remains the same as mentioned in step 3.

Through wafer Si etch from backside using Bosch process.

The cantilever is released by through wafer etching of Si using STS® inductively coupled plasma (ICP) etcher. We used 'Bosch process' where the etcher alternates between an 'etch' cycle and 'passivation' cycle. During the etch cycle, Si is isotropically etched using SF6 for 10 seconds, then the etched region is passivated with a polymer (C4F8) for 7 seconds in the passivation cycle. The whole process continues alternatively as long as the cantilever is not released, resulting in a high aspect ratio Si etch with vertical side walls.

Through Wafer Si Etch from Backside Using Bosch Process

The cantilever is released by through wafer etching of Si using STS® inductively coupled plasma (ICP) etcher, using a 'Bosch process' where the etcher alternates between an 'etch' cycle and 'passivation' cycle. During the etch cycle, Si is isotropically etched using $SF_6$ for 10 seconds, then the etched region is passivated with a polymer ($C_4F_8$) for 7 seconds in the passivation cycle. The whole process continues alternatively as long as the cantilever is not released, resulting in a high aspect ratio Si etch with vertical side walls.

However, the usual practice of processing this particular layer involves depositing thick $SiO_2$ on the back side which acts as the hard mask for Si etching. Then patterning with NR 71 resist (4 µm thick), the oxide is wet chemically etched using buffered oxide etchant (BOE). The resist is then removed from the backside and also from the top side (which acts as a protecting layer of the devices on the top side from spinner and buffered oxide etchant (BOE)). After that the sample is put into ICP to etch Si for releasing the cantilevers. This process is faster and easier, however there are several key factors that affect the final outcome. In ICP the selectivity is about 90:1 between Si and $SiO_2$. For a wafer of 500 μm thick (our first generation wafer from NITRONEX INC), the oxide needs to be 7-8 μm thick on the backside of the sample and also in the carrier wafer. The carrier wafer is needed for mounting small samples with cool grease before loading in the inductively coupled plasma (ICP) chamber. Now if the pocket (where the Si will be etched) is big enough and the layer has symmetric design with moderately thick Si substrate the above mentioned process works fine but will have lot of undesirable undercut of Si, resulting in over hanged cantilevers. As the maximum strain is supposed to be at the base and the cantilever should be the only suspended part, this process yields less sensitive devices and in some cases devices of no use. This process becomes totally inapplicable and impractical, in most embodiments, if:

(a) The thickness of Si wafer is above 600 μm, as the thickness of oxide would be more than 8 μm which would require longer tool time. Like our recent wafer which is 720-800 μm, the oxide thickness should be more than 10 μm. The PECVD tool allowed 3 μm thick film deposition at a time, but the quality becomes bad. So it is advised to deposit 2 μm thick oxide (50 nm/min deposition rate needs 40 minutes plus purging time yields about an hour), then run clean process for 2 hours and deposit again. That means more than 14 hours of total processing time is required from that tool.

(b) If the design has asymmetry with pocket size varying from 50 μm to 800 μm (the shorter side of the rectangular pocket or the diameter of a disc), the etch rate of Si in ICP will vary significantly as bigger pocket gets etched faster. Eventually it will take almost double the theoretical time (400 nm/cycle, each cycle is 17 seconds long) to completely release suspended structures from all the pockets. Most importantly BOE etching of that thick oxide with a large variety in pocket size is literally impossible to control, resulting in under-etched or over-etched $SiO_2$ mask and eventually a total mess after Si etching with that hard mask. The fabrication yield would be very low with this process.

(c) The tool time required for the ICP would be ~12 hours for releasing all the structures, assuming 1000 μm thick (taking into account for the different pocket sizes) Si and etch rate of 400 nm/cycle. That much deep Si etching would obviously result in a lot of undercut.

To account the above mentioned problems and to ensure higher fabrication yield with zero undercut in the microcantilevers, new process was designed. The details of this new process are described below:

Thinning Down of Bare Si Substrate:

To deal with ~800 μm thick Si, the samples were first thinned down in STS® inductively coupled plasma (ICP) using the Bosch recipe to make the thickness about 400 μm. The other recipe can be used just with $SF_6$ etch cycle with no passivation cycle which would be faster. However, selectivity ratio would be lower with $SiO_2$ (measured to be 40:1 instead of 90:1). But this does not affect anything at all as long as the carrier wafer has enough oxide (in this case the thickness was 9 μm). To mount the sample cool grease was used carefully on the top side, at the corners and open area outside 1.4 cm square box. As there will be no resist removal step in this whole process, unfortunately the top surface was not protected with any resist coating. Also the resist may get cross linked for this long duration of Si etching, so if possible the resist coating on the top surface should be avoided. Another important thing is, if the cool grease is not applied enough, the samples get very hot and metal layers get peeled off from the surface. So this step was done in intervals with 260 cycles runtime with 10 minutes pause. Total 760 cycles of the Bosch recipe was run to etch ~350-400 μm Si with an etch rate of ~500 nm/cycle (the etch rate is higher as bare Si was etched). The tool time was ~4 hours.

Oxide Deposition:

As the thinned down sample has become ~400 μm thick, so a total of 4 μm thick oxide was deposited in UNAXIS PECVD tool in two slots. After 2 μm deposition (50 nm/min) a clean process was run for 2 hours and the final 2 μm was deposited. Though from the selectivity 5 μm thick oxide seems necessary, but the photo resist would provide the extra etching cycles. Also, even if the oxide gets etched down but Si still remains unetched, the pattern would be already there, and the Si substrate would only get thinned down which will not harm anything. It is a good practice to prepare carrier wafer which would be the prime Si wafers or any clean Si wafer with at least 8 μm thick oxide. Each wafer should be used once in the ICP. The tool time was 2 hours and 40 minutes in UNAXIS PECVD and it is same in STS® plasma-enhanced chemical vapor deposition (PECVD) 2. But the later has better quality oxide than the former with only drawback is less number of samples can be loaded. If time permits, it is better to use the later tool to deposit oxide following the same procedure.

Photolithography:

The thinned down and oxide deposited sample was patterned with NR 5 photoresist. The reason for using NR 5 was its thickness, minimum being 8 μm (at 3000 rpm) and maximum being 100 μm (at 500 rpm). The resist acts as a mask not only for etching oxide but also during Si etching. The selectivity was found to be 1:1 with oxide in reactive ion etch (RIE) and 40:1 with Si in ICP. So there should about 4 μm resist left after etching oxide to cushion against etching the first 140-160 μm Si. That also helps in depositing thinner oxide film. However care should be taken to choose the thickness of the resist, as the resist gets thicker after development the profile does not remain steep and the resist loose its integrity for further processing. The optimized thickness was found to be 8 μm which gave good results. Up to 15-20 μm thickness would be fine with NR 5. Both NR 5 and NR 71 are good etch resist but NR 71 offers maximum thickness of 12-14 μm but is less reliable. The litho step is same as previous, but after the development oxygen plasma cleaning can be run for 1-2 minutes to ensure no resist film is remaining in the pockets. It is not mandatory as the ultimate etching time very long which would eventually etch down the thin resist residues.

Dry Etching of Oxide:

The 4 μm thick oxide was etched down using NR 5 as the mask in two slots with 2 μm film being etched every time and running a complete clean process for 3 hours in between in Plasma Therm RIE. The etch rate is 50 nm/min but overetching was done (assuming 5 μm thickness) to ensure complete etching of the oxide from the pocket. A gradient of color can be seen in open eyes up to 80-90 μm thickness. Then microscope could be used to ensure further etching. As the backside is rough so it becomes harder to justify if few nm film of oxide is remaining. However it will again not affect due to longer etching of Si. This tool usually makes the sample contaminated which however did not affect further processing, but it is highly recommended to use VISION® RIE for etching oxide. In that case, selectivity and etch rate should be measured. It is to be noted that, as the etching was done assuming 5 µm thick oxide, the remaining resist would be 3 µm, which would be good enough to support. Before optimizing the process, two samples were simultaneously processed but one was used in reactive ion etch (RIE) to etch oxide and the other one was etched with BOE to compare the results. After the etching, the damages due to BOE was visible but still it was processed further. The total tool time was ~4 hours.

Deep Si Etching with Bosch Process:

The samples (~400 µm thick Si substrate) were mounted on carrier wafer with sufficient cool grease. While applying grease with swab on the top surface, the nearby area surrounding the top pocket (where the GaN was etched) was avoided as the exposed cool grease (after etching Si) would deposit contaminated film and sputtered all over the sample. The Bosch recipe was used and the samples were processed for 1000-1200 cycles in slots of 250 cycles and 10 min pause in between, so that the samples do not get over heated. Over etching does not affect as GaN is barely etched with SF6 (about 200-300 nm). However, in the new wafer, the cantilever thickness is 1.1 µm after mesa etching. So care should be taken or this can aid in thinning down GaN slowly if different thickness of cantilever is required. Visual inspection would be enough to ensure complete etching and also the samples will be auto diced as per design. The total tool time in STS® ICP was ~6 hours.

The newly developed process offered the following advantages:

1. Absolutely no undercut, no overhang, and the fabrication yield is 100% with releasing about 1000 microcantilevers and suspended structure.

2. Total process time is about 18 hours including tool time and lithography process compare to 30 hours process time with previous process.

3. The usual process is absolutely not applicable with more complex design such as this which involve dense integration of microcantilevers.

4. No BOE handling at all which not only damages metal stack but also very dangerous if exposed to human body.

The epilayer GaN and Si(111) substrate has lattice mismatch and thermal expansion coefficient difference. Moreover during growth of GaN on Si (111) there is an internal stress distribution due to inhomogeneous outgrowth of the layer. This causes a residual tensile stress component in the epilayer. The residual stress in the GaN layer is influenced by growth conditions, layer thickness, and layer structures, as well as choice of substrate. However, during the release of the cantilever there is a change in stress which pulls the cantilever upwards resulting in curled up structures. The longer microcantilevers have more bending compared to the shorter ones.

Example 2

Total resistance of the HFET (externally measured), $R_{DS}=R_{int}+2R_C+2R_{acc}$, where $R_{acc}$ is the access region resistance, $R_c$ denotes the source and drain contact resistances. $R_{int}$ is the drain-source resistance of the intrinsic transistor, where the gauge factor, GF, can be derived as (derivation is given in the last section), $$GF = \frac{\frac{\Delta R_{DS}}{R_{DS}}}{\varepsilon} \approx -\frac{1}{\varepsilon}\left[\frac{\Delta \mu_{int}}{\mu_{int}} + \frac{\Delta n_{s,int}}{n_{s,int}}\right] \quad \text{(Equation 2.1)}$$

Here, $\mu_{int}$ and $n_{s,int}$ are the mobility and carrier concentration for the intrinsic device, and $\varepsilon$ is the average strain in the channel. It is obvious from Eqn. 2.1 that the GF depends on both changes in carrier concentration and mobility, which are strongly correlated at gate biases close to pinch-off (i.e. lower carrier concentration). Clearly, this results in a higher GF in a gated piezoresistor, where the gate voltage can be used to tune the carrier concentration to a desired (low) level where the mobility would change significantly due to change in carrier concentration, in addition to higher fractional change in the carrier concentration itself (caused by external strain). For a Si piezoresistor (i.e. p-type Si) the carrier concentration does not depend on external strain, so the additional benefit of mobility change, caused by change in carrier concentration as noted above, is absent.

In a simple AlGaN/GaN piezoresistor, without the possibility of gate modulation, the carrier concentration does change with strain but the additional advantage of mobility change is uncertain.

Step Bending

To determine the step bending response, the microcantilever was bent down by 1 µm and released, as VGS was systematically varied. Downward bending causes larger tensile strain in the AlGaN layer, which in turn, generates more positive piezoelectric charge at the AlGaN/GaN interface, drawing excess compensating electrons ($\Delta n_s$), and thereby reducing RDS. When the cantilever is released, excess tensile strain is reduced, and RDS returns to its initial value. With more negative $V_{GS}$ applied, $n_s$ reduces, which increases the ratio $\Delta n_s/n_s$ and maximizes $\Delta R_{DS}/R_{DS}$ and hence the GF. The step bending response of this device, for $V_{GS}=0$ and $-3.1$ V was found to be $R_{DS}=1$ kΩ and $\Delta R_{DS}=7\Omega$, whereas $V_{GS}=-3.1$ V yielded $R_{DS}=2.16$ MΩ and $\Delta R_{DS}=300$ kΩ. Thus, $\Delta R_{DS}/R_{DS}$ increased more by 2 orders as $V_{GS}$ approached the shutdown voltage of the HFET of $-3.2$ V. The computed sensitivity ($=\Delta R_{DS}/R_{DS}$) increases monotonically from $V_{GS}=0$, and reaches a maximum value of 13.8% at $V_{GS}=-3.1$ V. The average strain on the HFET was estimated as $4.3\times10^{-5}$ from the finite element COMSOL simulation. A maximum GF=3200 is calculated at $V_{GS}=-3.1$ V, which decreases monotonically as the $V_{GS}$ increases to more positive values. It is noteworthy that the maximum GF calculated here is 35 times higher than the optimized Si based piezoresistive devices (GF=95), and comparable to that of SWCNT (GF=2900). The sensitivity of this device did not vary significantly with $V_{DS}$. However, with more negative $V_{GS}$, especially near shutdown, the HFET was operated in the saturation region to enable $I_{DS}$ to dominate over the gate leakage current. Although significant transients were observed for more negative $V_{GS}$ when the cantilever was bent down and released, we only considered the steady state values of $R_{DS}$ for calculating GF. If the maximum transient value of $R_{DS}$ is used we would get a much higher GF of about 10,000. It is possible that if the transients are minimized through proper device passivation then even higher GF can be achieved.

Dynamic Bending

For dynamic response, an oscillating piezochip was contacted to the DIP, which generated a surface wave that propagated to the cantilever to initiate oscillation. The oscillation of the microcantilever was transduced by the HFET (biased with constant $I_{DS}$=10 µA and $V_{GS}$=−2.3 V), where the $R_{DS}$ changed periodically, resulting in a periodic change in the drain-source voltage, $\Delta V_{DS}$, which was measured by the lock-in amplifier. Laser vibrometer measurements very closely matched the HFET measurements, which yielded a resonant frequency of 43.94 kHz with a quality factor of 230. The voltage responsivity (VR) which is a more important parameter than GF for dynamic bending, was determined by taking the ratio of $\Delta V_{DS}$ and the oscillation amplitude considering the difference of the on-resonance peak and off-resonance base. Comparing the two measurements, we find that a change in oscillation amplitude of 7.9 nm (from vibrometer) corresponded to $\Delta V_{DS}$ (rms)=7.5 µV (from HFET). Thus, the VR can be calculated as 0.95 µV/nm. Similarly as in step bending case, more negative $V_{GS}$ resulted in increased $\Delta R_{DS}$ which enhanced the responsivity, since $\Delta V_{DS}=I_{DS} \times \Delta R_{DS}$. With decrease in $V_{GS}$, VR increases monotonically, reaching a value of 40 µV/nm with the same piezo excitation, at $V_{GS}$=−2.7 V and $I_{DS}$=10 µA. The power dissipation across the HFET was calculated using $P_{DS}=I_{DS}^2 \times R_{DS}$ for different $V_{GS}$ using $I_{DS}$=10 µA and $R_{DS}$ values. It was found that $P_{DS}$ increases monotonically from 0.51 µW to 2.4 µW, as $V_{GS}$ becomes more negative, changing from −2.3 V to −2.7 V. The piezoresistive response of the HFET is limited mainly by the Johnson noise at high frequency which is given by, $S_J=\sqrt{(4k_B T R_{DS} B)}$, where $k_B T$=26 meV at room temperature and B is the measurement bandwidth. With B=10 Hz, the calculated Johnson noises were 28.84 nV and 139.42 nV for $V_{GS}$=−2.3 V and −2.7 V, respectively, while the corresponding signal-to-noise ratios (SNR=20 $\log_{10}$ (VR/$S_J$)) are 30.35 dB and 49.15 dB, for 1 nm oscillation amplitude. However changing the bias current from 10 µA to 100 µA, sharply increased the SNR from 30.35 dB to 73.7 dB. Clearly, there is a trade-off between three critical parameters of a HFET deflection transducer, namely, power dissipation, responsivity and SNR. For example, for $V_{GS}$=−2.3 V, we obtained the highest responsivity of 140 µV/nm with an SNR of 73.7 dB, however this was achieved at the cost of higher power dissipation of 51 µW. We would like to mention here that this device and other similar devices have shown excellent repeatable and reproducible performances as mentioned above when tested several times in one year time period.

Our gated piezoresistor offers the advantage of utilizing the same device to cater to various application needs (i.e. requirement of low power consumption, high sensitivity, high SNR, or DC to ultrasonic frequency operations), simply by biasing the transistor. The experimental results presented here provide the necessary insights into the operation of HFET embedded micro/nano cantilever.

Rectangular Microcantilever Device Performance

One of the newly fabricated microcantilevers (length is 150 µm, width 50 µm and thickness is 1 µm) was tested. Impressive and better performances were observed. The transmission line measurement (TLM) results on TLM pads which yielded contact resistance of 13.39Ω and sheet resistance of 478.1Ω/□. The device also showed excellent gate control and very high current with low leakage as expected from usual AlGaN/GaN HFET. Similar as described earlier, static bending test was performed and the device presented 140% change in HFET channel resistance for 10 µm bending.

Triangular Microcantilever Device Performance

One of the newly fabricated triangular microcantilevers (V shaped, height 250 µm, width 60 µm, and thickness 1 µm) was also studied with both static bending and dynamic bending characterizations. The V shaped cantilevers have two arms and so two HEFT with similar or different orientations considering current conduction, were integrated. However the chosen one was with two similar HFETs. Two of the HFETs were either used together or separately to transduce the mechanical deflection of the V shaped Microcantilever. In that case the biasing parameters were kept same for both HFETs when acted as a single HFET. The channel resistances ($R_{DS}$) were measured to be 850Ω and 1.2 kΩ for the devices. As described earlier, the higher the resistance, the higher the sensitivity (or gauge factor), so it is presumed that HFET with the higher resistance will present higher sensitivity. However, as we have separate gate controls we can tune the gate bias to match the resistances to obtain equal sensitivity. The mechanical arms are symmetrical, so if the external stress is applied in the middle of the tip equal strain would be distributed at the two bases yielding equal piezoresistive changes. However in this experiment we have kept the drain-source and gate bias same and the cantilever was bent 1 µm downward and released. The bending results were analyzed, when the two HFET transduced separately, and when they were connected together externally (with jumper cables shorting two sources and drains). The sensitivities were measured to be 0.44% (for one HFET), 0.57% (for the other HFET), and 0.48% (both) per 1 µm.

The dynamic responses were also measured with this cantilever as described earlier (the measurement). The cantilever was oscillated with Piezo actuation. The resonance frequency was found 47.871 kHz and the quality factor was 371. Fortunately there was a dust particle on the cantilever which allowed us to measure the mass loading on the microcantilever and the corresponding frequency shift, which the frequency downshift of the resonance frequency of the cantilever was found to be by 721 Hz when a dust was on the cantilever. The bias optimization was not performed on this particular cantilever. But the biasing parameters were: constant $I_{DS}$=10 µA, VGS=−3.0 V.

Example 3

The ultrahigh deflection sensitivity achieved using an AlGaN/GaN heterojunction FET (HFET) embedded piezotransistive GaN microcantilever was demonstrated, which resulted in successful transduction of femtometer level displacement at the resonance frequency of the cantilever. The capability of measuring these extremely small displacements, verified independently through laser vibrometry studies, has enabled detection of nanogram level explosives with high specificity using novel surface based photoacoustic technique.

Piezotransistive microcantilevers were fabricated using III-Nitride epitaxial layers grown on Si (111) substrate. The overall layer structure was i-GaN (2 nm)/AlGaN (17.5 nm, 26% Al)/i-GaN (1 µm)/Transition layer (1.1 µm)/Si (111) substrate (500 µm), wherein "i-type semiconductor" indicates "undoped semiconductor" or "intrinsic semiconductor". The HFET was fabricated with initial 200 nm mesa etching followed by GaN cantilever pattern etched down using $BCl_3/Cl_2$ based inductively coupled plasma etch process. Ohmic contacts were formed with Ti (20 nm)/Al (100 nm)/Ti (45 nm)/Au (55 nm) metal stack deposition and rapid thermal annealing. Schottky gate contact was then formed with Ni (25 nm)/Au (375 nm) deposition. Finally, through wafer Si etch was performed by "Bosch process" to release of the microcantilevers.

Detection of Nanoscale Static Deflection

The fabricated microcantilevers had dimensions of 250× 50×2 µm³, with the embedded HFET's channel dimension being 17×29×6 µm³. Each chip had 4 similar microcantilevers, which were wire bonded to a 28 pin dual-in-line package (DIP) chip carrier. Apart from the conventional source, drain, and gate contacts of the HFET, there was an additional contact for electrostatic actuation of the microcantilever, which was not used in this study. Typical IDS-VDS and IDS-VGS characteristics of the HFET, exhibiting good gate control. Utilizing a negative gate bias the piezoresistive effect was translated into a piezotransistive effect where the 2DEG carrier concentration (ns) 140 was reduced, thus increasing the $\Delta ns/ns$ ratio ($\Delta ns$ is the change in 2DEG density due to strain caused by deflection of the cantilever).

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed is:

1. A microcantilever based photoacoustic sensor, comprising:
   a substrate;
   a GaN layer on the substrate, wherein the GaN layer defines a microcantilever extending beyond an edge of the substrate, with a base area of the microcantilever defined by the edge of the substrate, wherein the microcantilever is encapsulated by a sapphire window and within a vacuum;
   a heterojunction field-effect transistor (HFET) deflection transducer positioned on the microcantilever;
   a pair of electrical contacts, each electrically connected to the HFET deflection transducer; wherein the HFET deflection transducer positioned on the microcantilever has a cross-section comprising the following layers arranged in consecutive horizontal order:
   a buffer layer directly on the substrate;
   the GaN layer directly on the buffer layer, wherein the GaN layer is undoped;
   an AlN layer directly on the GaN layer;
   an AlGaN layer directly on the AlN layer; and
   an additional undoped GaN layer directly on the AlGaN layer; and
   at least one microfluidic channel on the base area and in fluid communication with an analyte reservoir, wherein the analyte reservoir is positioned on the base area and adjacent to the microcantilever;
   wherein the microcantilever based photoacoustic sensor has a gauge factor rater than 4500.

2. The microcantilever based photoacoustic sensor of claim 1, further comprising:
   wherein the sapphire window is positioned over and encapsulates the at least one microfluidic channel.

3. The microcantilever based photoacoustic sensor of claim 1, wherein the at least one microfluidic channel and the reservoir are defined by surfaces coated with a poly(p-xylylene) polymer.

4. The microcantilever based photoacoustic sensor of claim 1, wherein the substrate comprises silicon.

5. The microcantilever based photoacoustic sensor of claim 1, wherein the microcantilever has a length of from 50 µm to 300 µm, a width of from 25 µm to 100 µm, and a thickness of from 0.5 µm to 1.5 µm.

6. The microcantilever based photoacoustic sensor of claim 1, wherein the substrate comprises silicon, and wherein the buffer layer has a thickness from 0.5 µm to 2.5 µm on the substrate, and further wherein the GaN layer has a thickness from 500 nm to 2 µm.

7. A sensing system comprising:
   the microcantilever based photoacoustic sensor of claim 1; and
   a pulsed infrared laser positioned to direct infrared electromagnetic radiation into the analyte reservoir of the microcantilever based photoacoustic sensor.

* * * * *